United States Patent
Robb et al.

(10) Patent No.: US 10,301,619 B2
(45) Date of Patent: May 28, 2019

(54) COMPOSITIONS AND METHODS RELATING TO SYNTHETIC RNA POLYNUCLEOTIDES CREATED FROM SYNTHETIC DNA OLIGONUCLEOTIDES

(71) Applicant: New England Biolabs, Inc., Ipswich, MA (US)

(72) Inventors: G. B. Robb, Somerville, MA (US); Isaac B. Meek, Hopkinton, MA (US); Dianne S. Schwarz, Watertown, MA (US); Ezra Schildkraut, Cerillos, NM (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 15/469,681

(22) Filed: Mar. 27, 2017

(65) Prior Publication Data
US 2017/0283797 A1     Oct. 5, 2017

Related U.S. Application Data

(60) Provisional application No. 62/317,035, filed on Apr. 1, 2016.

(51) Int. Cl.
| | | |
|---|---|---|
| *C12P 19/34* | (2006.01) | |
| *C12N 15/10* | (2006.01) | |
| *C12N 9/22* | (2006.01) | |
| *C12N 9/96* | (2006.01) | |
| *C12N 15/115* | (2010.01) | |
| *C12Q 1/68* | (2018.01) | |

(52) U.S. Cl.
CPC .......... *C12N 15/1068* (2013.01); *C12N 9/22* (2013.01); *C12N 9/96* (2013.01); *C12N 15/115* (2013.01); *C12P 19/34* (2013.01); *C12N 2310/16* (2013.01); *C12N 2310/20* (2017.05); *C12N 2320/13* (2013.01); *C12N 2330/00* (2013.01); *C12N 2330/31* (2013.01); *C12Q 1/68* (2013.01)

(58) Field of Classification Search
None
See application file for complete search history.

(56) References Cited

U.S. PATENT DOCUMENTS 8,039,214 B2 * 10/2011 Dahl ................. C12N 15/1096
435/6.11
2016/0215328 A1 * 7/2016 Kazakov ............. C12Q 1/6837

OTHER PUBLICATIONS

Svensen, et al., Cell Chemical Biology, 23:415-25, 2016.
Jinek, et al., Science, 337, 6096:816-21, 2012.
Esvelt, et al., Nature Methods 10: 1116-112, 2013.
Zetsche, et al., Cell. 163: 1-22, 2015.
Dolgosheina, et al. ACS Chem Biol., 9: 2412-2420, 2014.
You, et al., Annu Rev Biophys., 44: 187-206, 2015.
Filonov, et al., Chem Biol. 22:649-660, 2015.

* cited by examiner

*Primary Examiner* — Celine X Qian
(74) *Attorney, Agent, or Firm* — New England Biolabs, Inc; Harriet M. Strimpel

(57) ABSTRACT

Compositions and methods are provided for forming a single RNA polynucleotide from a plurality of DNA oligonucleotides in a single reaction chamber using combined reagents in a single step reaction. DNA polymerase, RNA polymerase and single stranded (ss) DNA oligonucleotides are combined where each DNA oligonucleotide has one or more sequence modules, wherein one sequence module in the first ss DNA oligonucleotide is complementary to a sequence module at the 3' end of the second ss DNA oligonucleotide; and wherein a second module on the first ss DNA oligonucleotide is an RNA polymerase promoter sequence; and forming a single RNA polynucleotide, excluding the RNA promoter sequence, derived from the first and second DNA oligonucleotides.

8 Claims, 13 Drawing Sheets
Specification includes a Sequence Listing.

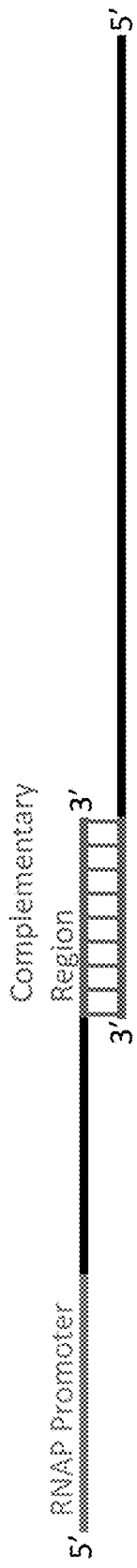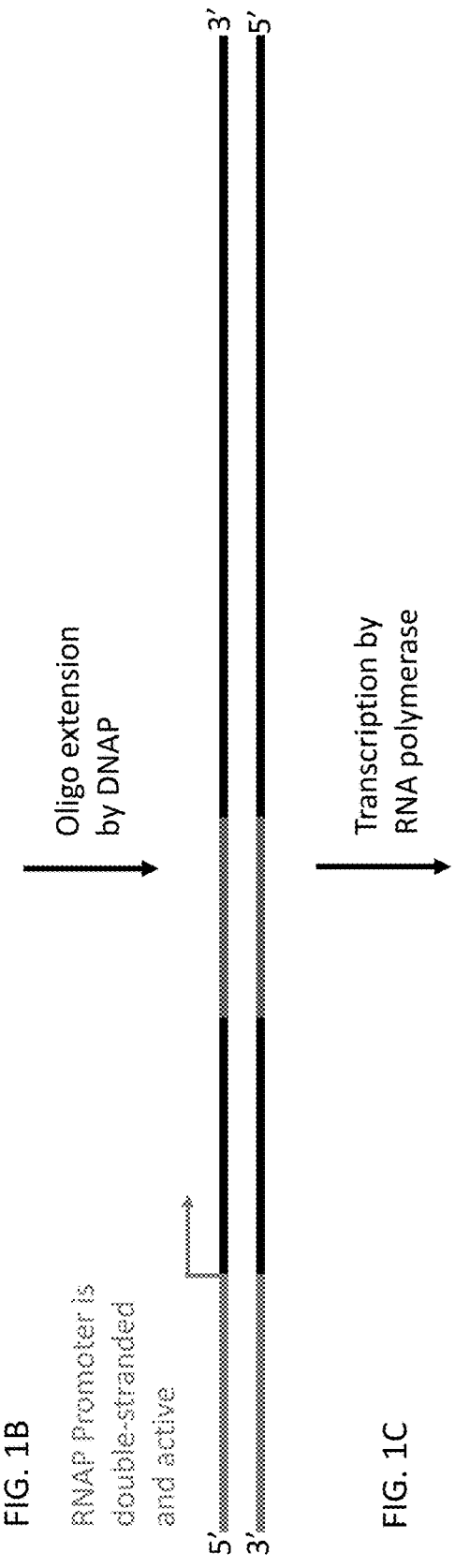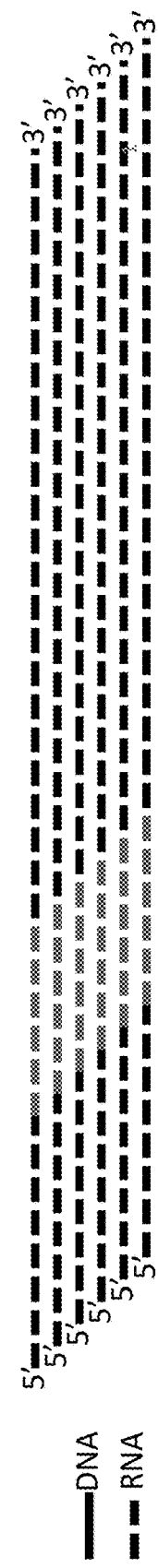

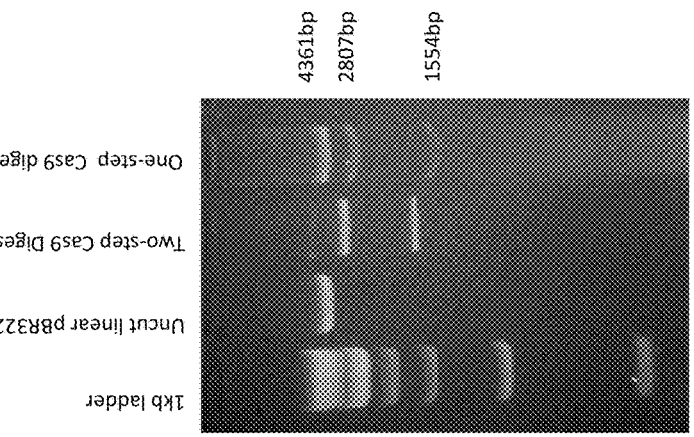
FIG. 2F
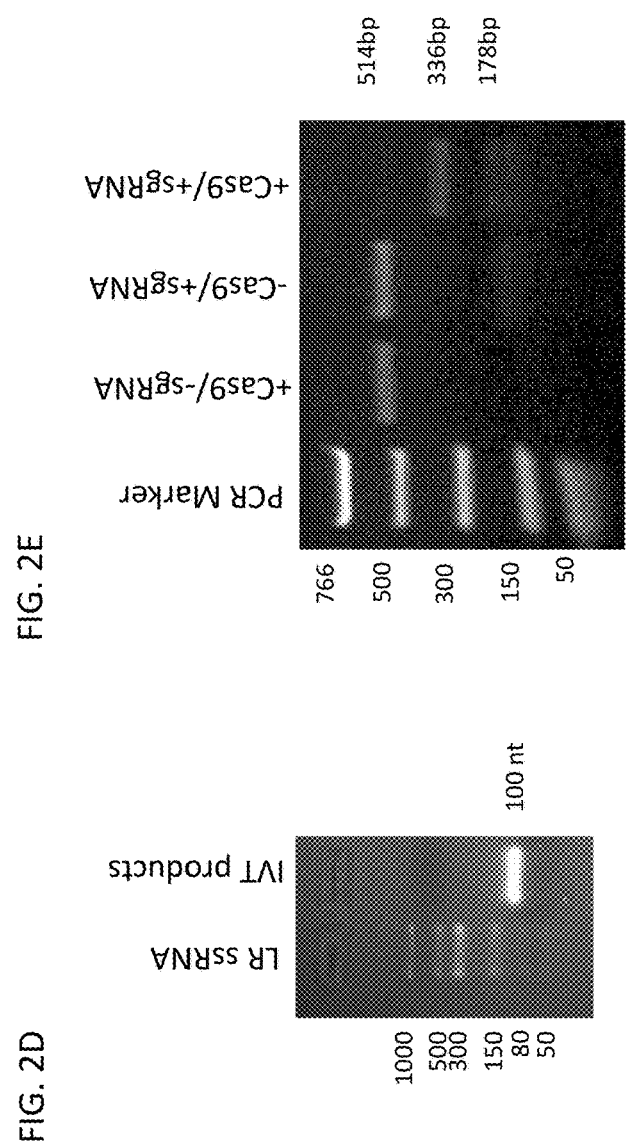
FIG. 2E
FIG. 2D

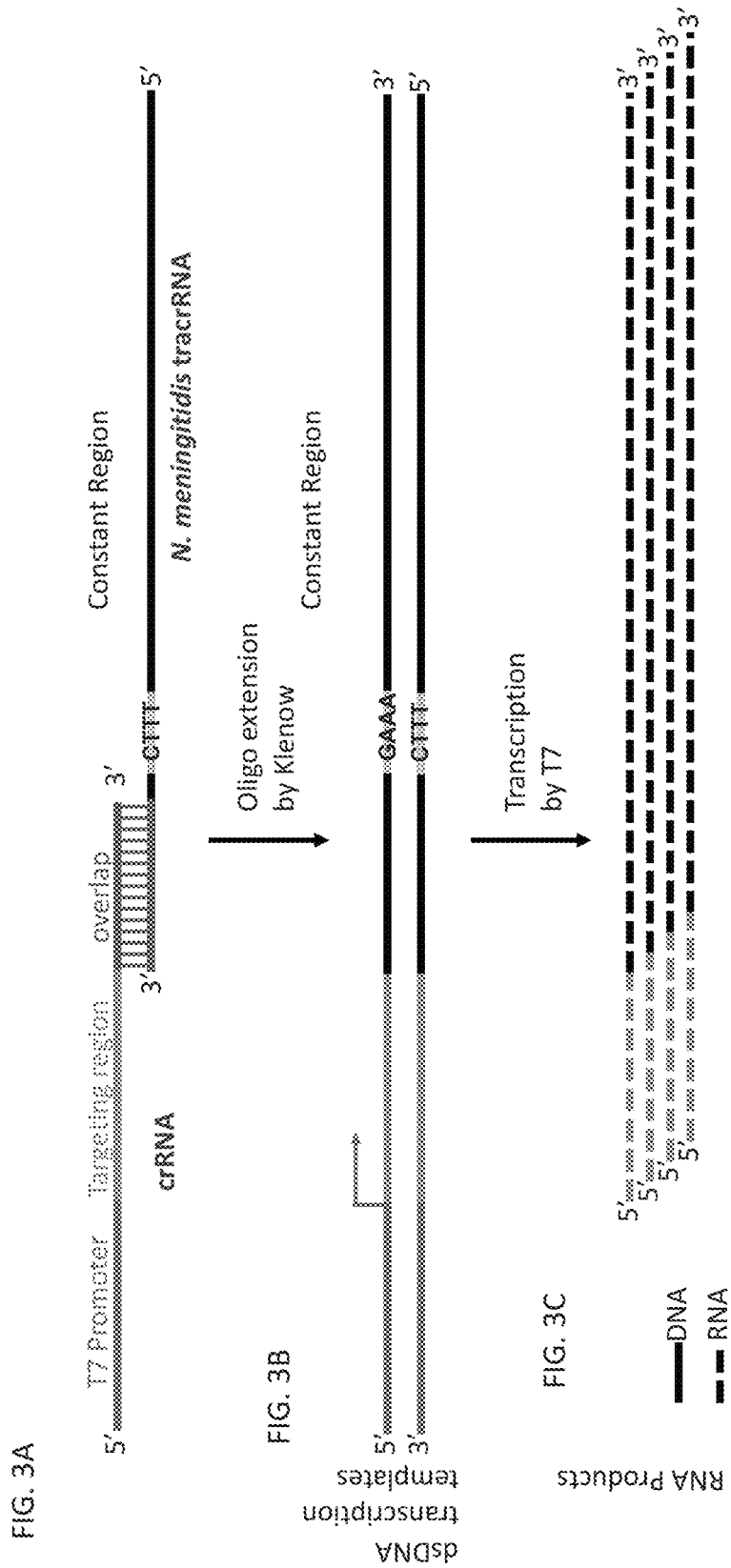

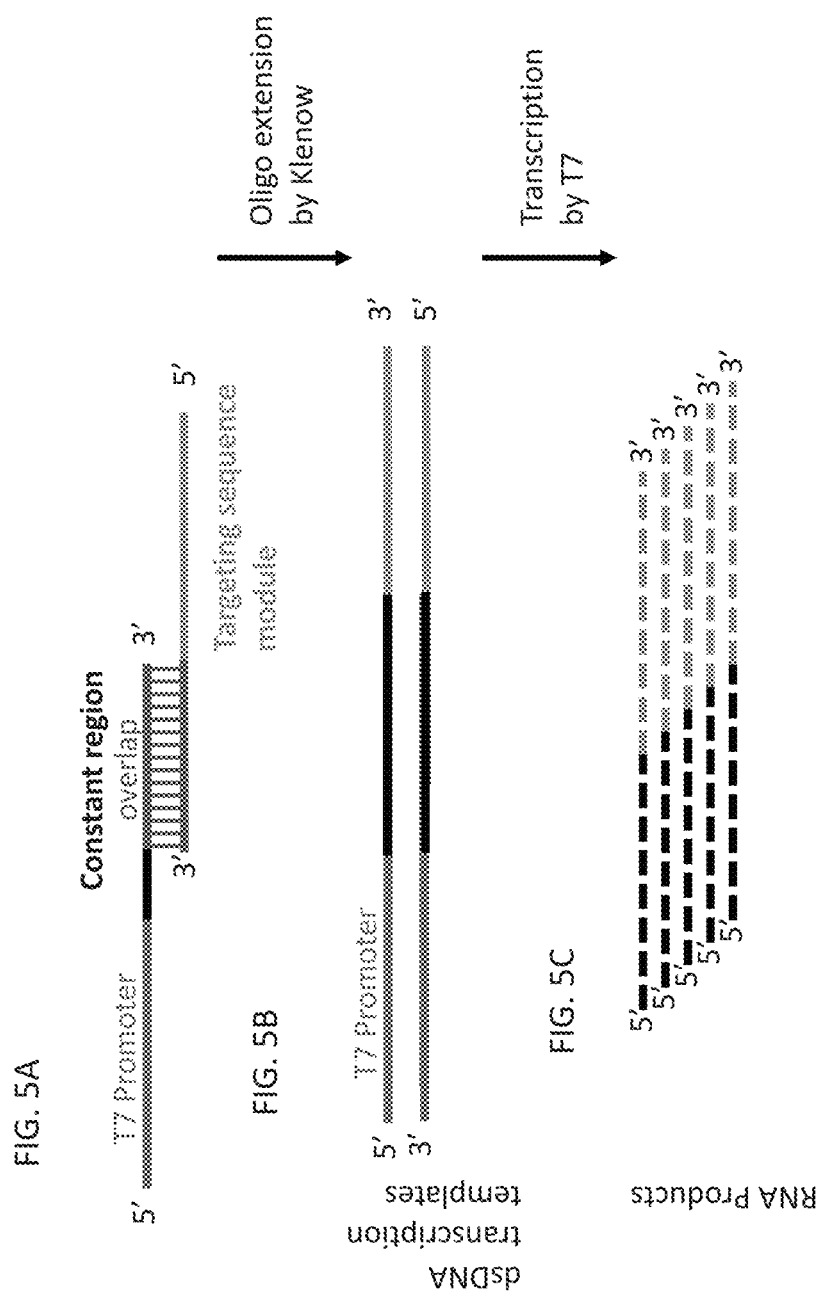

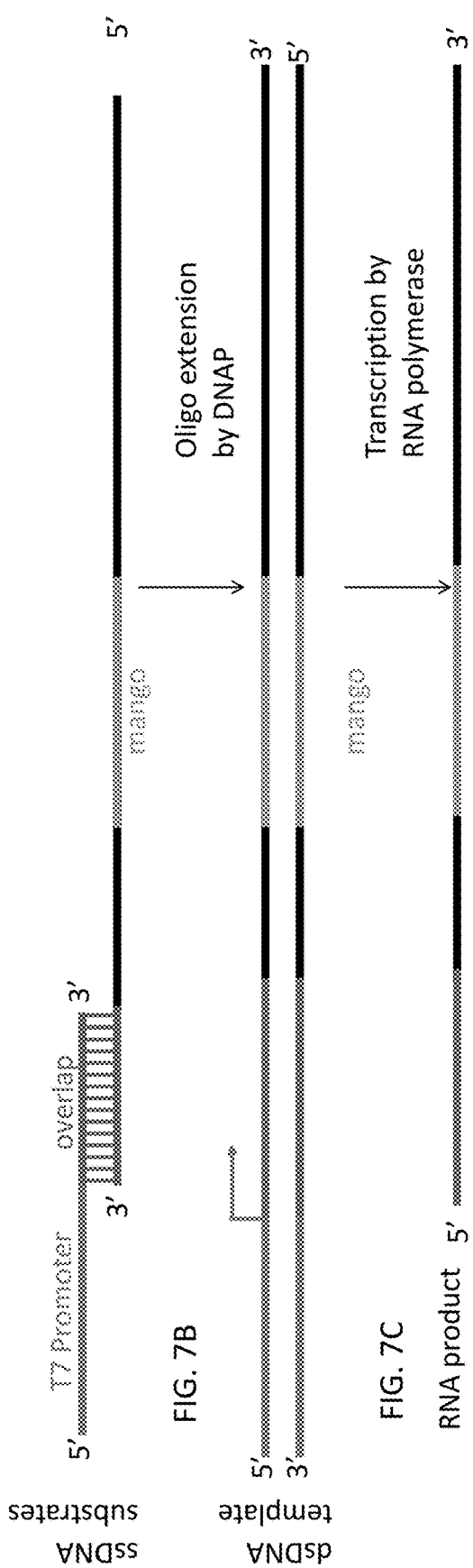
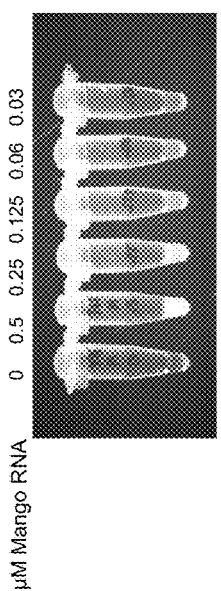
FIG. 7A
FIG. 7B
FIG. 7C
FIG. 7D

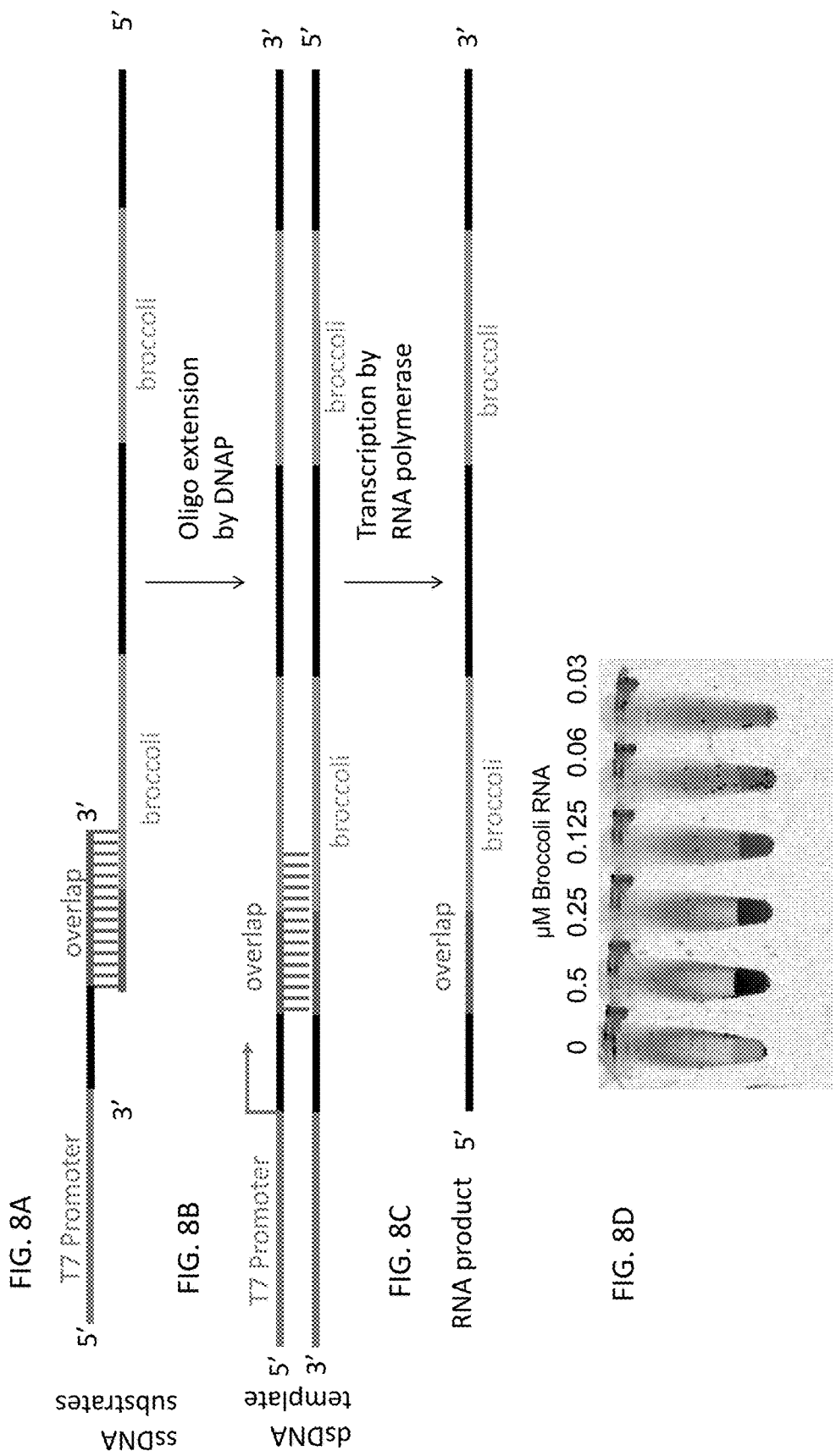

COMPOSITIONS AND METHODS RELATING TO SYNTHETIC RNA POLYNUCLEOTIDES CREATED FROM SYNTHETIC DNA OLIGONUCLEOTIDES

CROSS REFERENCE

This application claims right of priority to U.S. provisional application Ser. No. 62/317,035 filed Apr. 1, 2016.

BACKGROUND

While amplification of target genomic DNA or cDNA in a library to generate adapter linked DNA that can be copied by RNA polymerases is routinely performed, preparation of synthetic RNA polynucleotides de novo involves a series of reactions which can involve multiple steps and is quite cumbersome. Recently with increasing need to manufacture and study larger RNA polynucleotides including guide RNAs and mRNAs, it is desirable to improve the efficiency of the synthetic methodologies.

SUMMARY

In general in one aspect, a preparation is provided in a single reaction vessel, that includes: (a) a first and a second synthetic single strand (ss) DNA oligonucleotide each containing a plurality of sequence modules, wherein the first synthetic oligonucleotide comprises a 5' end and a 3' end, and wherein one sequence module is positioned at the 3' end of the first oligonucleotide that hybridizes to a complementary sequence module at the 3' end of the second oligonucleotide; and a second sequence module on the first oligonucleotide corresponds to an RNA promoter sequence; (b) a DNA polymerase capable of extending the 3' end of the first oligonucleotide and the 3' end of the second oligonucleotide in a 5' direction to produce a double stranded (ds) DNA; and (c) an RNA polymerase (RNAP).

In one aspect, a Cas nuclease is included in the preparation. In another aspect, the first oligonucleotide contains a sequence module in which the sequence is variable or the first or second oligonucleotide contains a sequence module in which the sequence is variable. The variable sequence may correspond to a sequence that is complementary to a DNA targeting sequence on a guide RNA.

In another aspect, the first or second oligonucleotide contains a sequence module corresponding to a sequence that is complementary to tracrRNA.

In another aspect, the hybridizing sequence of the first oligonucleotide is less than 15 nucleotides and/or the non-hybridizing sequence of the first oligonucleotide is at least 15 nucleotides. In another aspect, the second oligonucleotide sequence has a non-hybridizing sequence, wherein the non-hybridizing sequence of the second oligonucleotide is at least 15 nucleotides. In another aspect, a third synthetic oligonucleotide is provided having a predetermined sequence and a fourth synthetic oligonucleotide with a predetermined sequence, wherein the 5' end of the third synthetic oligonucleotide hybridizes to the 5' end of the second oligonucleotide and the 3' end of the third oligonucleotide hybridizes to the 3' end of the fourth oligonucleotide.

In another aspect, the DNA polymerase is a strand displacing polymerase and in another aspect the preparation includes a DNA ligase where three or more oligonucleotides are assembled together.

In another aspect, at least one of the first, second, third or fourth oligonucleotide comprise a sequence module that is a first detector molecule that when transcribed by the RNAP and combined with a second detector molecule such as a second sequence module on the first, second, third or fourth oligonucleotide, causes a detectable signal. An example of a first detector molecule is an aptamer sequence and of the second detector molecule is a fluorescent dye. An example of an aptamer sequence is mango or broccoli. In one aspect, the 5' end of the first oligonucleotide is immobilized on a solid support. In another aspect, the 5' end of the oligonucleotide includes a sequence module containing a modified nucleotide. In another aspect, the modified nucleotide is biotin or desthiobiotin.

In general, in one aspect, a method is provided of forming a single RNA polynucleotide from a plurality of DNA oligonucleotides in a single reaction chamber in a single step reaction, that includes: combining at least a first and second synthetic ss DNA oligonucleotide, each having one or more sequence modules, wherein one sequence module in the first ss DNA oligonucleotide is complementary to a sequence module at the 3' end of the second ss DNA oligonucleotide; and wherein a second module on the first ss DNA oligonucleotide is an RNAP promoter sequence; and forming a single RNA polynucleotide derived from the first and second DNA oligonucleotides excluding the RNAP promoter. In one aspect, the polymerase is the Klenow fragment of *E. coli* DNA polymerase I.

In one aspect, the single RNA polynucleotide is a guide RNA. In another aspect, a Cas nuclease capable of being activated in the presence of the guide RNA is included in the reaction chamber or is added after the single RNA polynucleotide is formed. Examples of single RNA polynucleotides formed by the method include an RNA selected from the group consisting of a guide RNA, an aptamer, a mRNA, a tRNA, a microRNA, a shRNA, an snRNA, a short non-coding RNA, a long non-coding RNA, an RNA probe, and a ribozyme.

In one aspect, a third and fourth synthetic ss DNA oligonucleotide may be included in the reaction chamber. The third synthetic ss DNA oligonucleotide may have a sequence module at the 5' end that hybridizes to the 5' end of the second ss DNA oligonucleotide. The 3' end of the third ss DNA oligonucleotide may include a sequence module that hybridizes to the 3' end of the fourth ss DNA oligonucleotide. The polymerase may fill-in the hybridized first, to fourth ss DNA oligonucleotide to form a duplex DNA which can be transcribed to form a single RNA polynucleotide that does not include the RNA promoter sequence. The method is not intended to be limited to four ss DNA oligonucleotides. In addition to assembling two or four ss DNA oligonucleotides described above, it is possible to utilize any number of odd or even numbered oligonucleotides beyond 2 oligonucleotides as desired.

If the polymerase is capable of strand displacement (such as Bst polymerase, Bst large fragment or Bst mutants, Deep Vent® polymerase, Vent® polymerase, Klenow fragment of *E. coli* DNA polymerase I (all commercially available from New England Biolabs, Ipswich, Mass.)), an intact duplex will be formed. If the polymerase is not capable of strand displacement (for example, Phusion® (Thermo Fisher Scientific), T7 DNA polymerase, T4 DNA polymerase, Taq polymerase (all commercially available from New England Biolabs, Ipswich, Mass.)) it will be desirable to include a ligase to repair nicks in order to create a full length intact duplex DNA from which an RNA can be transcribed.

In another aspect, a sequence module in the single RNA polynucleotide is a reactor sequence such as an aptamer, such as mango or broccoli, capable of combining with a detector molecule such as a fluorescent dye or a second aptamer, to give a detectable signal. Alternatively, the detector molecule may be another sequence module in the single RNA polynucleotide.

In one aspect, the RNA polynucleotide is immobilized on a solid support. In another aspect, the 5' end of the RNA polynucleotide contains a modified nucleotide for example, biotin or desthiobiotin.

In one aspect, the first ss DNA oligonucleotide contains a sequence module that contains a variable sequence. The RNA polynucleotide may be a guide RNA for Cas nuclease and the variable sequence may include a sequence suitable for targeting a DNA or RNA.

In one aspect, a library of first or second ss DNA oligonucleotides are provided in the method where substantially each member of the library has a different variable sequence module. Each reaction chamber assembled in an array contains one of these members. If the variable sequence module is in the first ss DNA oligonucleotide, a second ss DNA oligonucleotide, a DNA polymerase, an RNAP and optionally a Cas nuclease are also added to each reaction chamber in the array. At least one of the ss DNA oligonucleotides further includes a sequence module corresponding to a tracrRNA sequence to allow the RNA polynucleotide to interact with the Cas nuclease, activating the Cas nuclease to guide it to its target and enable it to cleave. The RNA polynucleotides in the library associated with Cas can then be tested to determine which if any binds a desired sequence in a genome.

In general in one aspect, a method is provided for making an RNA chimera from a plurality of synthetic DNA oligonucleotides, that includes (a) hybridizing overlapping sequences of synthetic DNA oligonucleotides; wherein (i) the 3' end of a first synthetic DNA oligonucleotide hybridizes to a 3' end of a second synthetic oligonucleotide; and the 5' end of the first oligonucleotide comprises a non-hybridizing sequence, containing an RNA promoter; (ii) optionally the 3' end of a third oligonucleotide hybridizes to the 3' end of a fourth oligonucleotide; (b) extending by means of a polymerase, the 3' ends of each oligonucleotide in a 5' direction to produce ds DNA; and (c) transcribing the ds DNA with an RNAP to form an RNA chimera. Examples of an RNA chimera might include part or all of one or more the following: a guide RNA, an aptamer, a mRNA, a tRNA, a microRNAs a shRNA, an snRNA, a short non-coding RNA, a long non-coding RNA, an RNA probe, and a ribozyme.

In general in one aspect a method is provided for making an RNA guided protein that includes using the methods described herein to make a single RNA polynucleotide derived from at least two DNA oligonucleotides using the methods described above.

In general in one aspect, a kit is provided that includes a single oligonucleotide which is preferably a synthetic DNA oligonucleotide and which has a sequence module at its 3' end that is capable of hybridizing to an overlapping complementary 3' sequence of a customer selected synthetic DNA having a sequence which when transcribed into RNA is capable of targeting a DNA sequence of interest. An RNA polymerase specific promoter may be positioned within the single DNA oligonucleotide. The kit may also contain a DNA polymerase capable of extending the 3' end of the oligonucleotides to produce double stranded DNA and also an RNA polymerase to transcribe the DNA These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

FIG. 1A-1C shows a schematic representation of the assembly and transcription in a single reaction of two ss DNA oligonucleotides with modular sequences. An advantage of combining a plurality of components is that one component may be varied and the other remain constant so that using permutations and combinations, it is possible to create a single designer RNA or create a library of RNA molecules.

FIG. 1A shows two synthetic ss DNA oligonucleotides where the first ss DNA oligonucleotide contains the promoter and partial coding strand of a ds DNA that serves as a template for transcription to form a chimeric RNA. The first ss DNA oligonucleotide also has a sequence at the 3' end that is complementary to the 3' end of a second oligonucleotide. The second ss DNA oligonucleotide contains the 3' complementary sequence that is part of the partial template strand. Extension of the first and second ss DNA oligos by DNA polymerase creates a complete coding strand and a complete template strand. The resulting ds DNA is the template molecule for transcription of the chimeric RNA. The "coding" strand and the "template strand" that form the ds DNA template molecule are terms of art referring to the RNAP and transcription. The coding strand may also be referred to as the "top" strand and has a sequence corresponding to all or part of the final RNA transcript. The "template" strand may also be referred to as the bottom strand and represent a sequence that is complementary to all or part of the final RNA transcript.

FIG. 1B shows ds DNA formed by extension of the 3' ends of each ss DNA oligonucleotide. The first oligonucleotide is the template for the DNA polymerase that extends the 3' end of the second oligonucleotide and vice versa. The region of the synthetic DNA corresponding to the RNAP promoter becomes active for transcription as soon as the ds DNA is formed.

FIG. 1C shows that the chimeric RNA polynucleotides are transcribed rapidly and accurately by the RNAP from the template strand in the DNA duplex. Transcription occurs as soon as the ds promoter is formed in the reaction.

FIG. 2A-2F shows how the assembly reaction in FIG. 1 can be applied to making custom guide RNA in a single reaction suitable for activating a *S. Pyogenes* Cas9 protein.

FIG. 2A shows a first ss DNA oligonucleotide containing a variable region inserted (which encodes a targeting region of a single guide RNA (sgRNA)) between a T7 RNA promoter and a complementary region for hybridizing with a second synthetic ss oligonucleotide. The first ss DNA oligonucleotide includes a module sequence for T7 RNAP promoter required for transcription of adjacent DNA sequence. Also included is a variable sequence module which is part of the coding strand of the final template. The second ss DNA oligonucleotide includes a module sequence for tracrRNA required for a functional single guide RNA.

FIG. 2B shows the ds DNA product of the 3' extension reaction of both synthetic ss oligonucleotides that contains sequences for the T7 RNA promoter, the variable region and the tracrRNA.

FIG. 2C shows transcription of ds DNA to form a single guide RNA. Transcription begins at the 3' end of the top strand of the T7 promoter.

FIG. 2D shows the products of the reaction detailed above after treatment with DNAseI and purification. Products were separated on a 2% agarose gel, and photographed under UV transillumination. The first lane contains an RNA molecular size standard (Low range (LR) ss RNA). The second lane contains the purified sgRNA (in vitro transcription (IVT) products) from the reaction.

FIGS. 2E and 2F show the specific ds DNA endonuclease activity of S. pyogenes Cas9 ribonucleoprotein programmed with a single guide RNA produced as outlined in FIG. 2A-2C.

In FIG. 2E, the substrate is a ~514 bp PCR product that is digested into 2 fragments of ~336 and ~178 bp after incubation with sgRNA programmed Cas9 protein in a 2 step reaction. Cas9 nuclease was programmed in vitro using purified reaction products depicted in FIG. 2A-D. Cleavage reactions were resolved on 1% agarose TBE gels, stained with ethidium bromide and photographed under UV transillumination.

The first lane contains a ds DNA ladder (PCR marker) with sizes as indicated.

The second lane contains target DNA incubated with Cas9 protein but no guide RNA (+Cas9/–sgRNA).

The third lane contains target DNA incubated with purified sgRNA products detailed in Example 1 but no Cas nuclease (–Cas9/+sgRNA).

The fourth lane contains target DNA incubated with Cas9 protein that was previously incubated with purified sgRNA products as detailed in Example 1 (+Cas9/+sgRNA).

In FIG. 2F, the substrate is a ~4361 bp linearized plasmid DNA that is digested into 2 fragments of ~2807 and ~1554 bp after incubation with sgRNA programmed Cas9 protein. Cleavage reactions were resolved on 1% agarose TBE gels, stained with ethidium bromide and photographed under UV transillumination.

The first lane contains a ds DNA ladder with sizes as indicated (1 kb ladder).

The second lane contains target DNA without digestion (uncut linear PBR322).

Figures 2A, 2B, 2C:
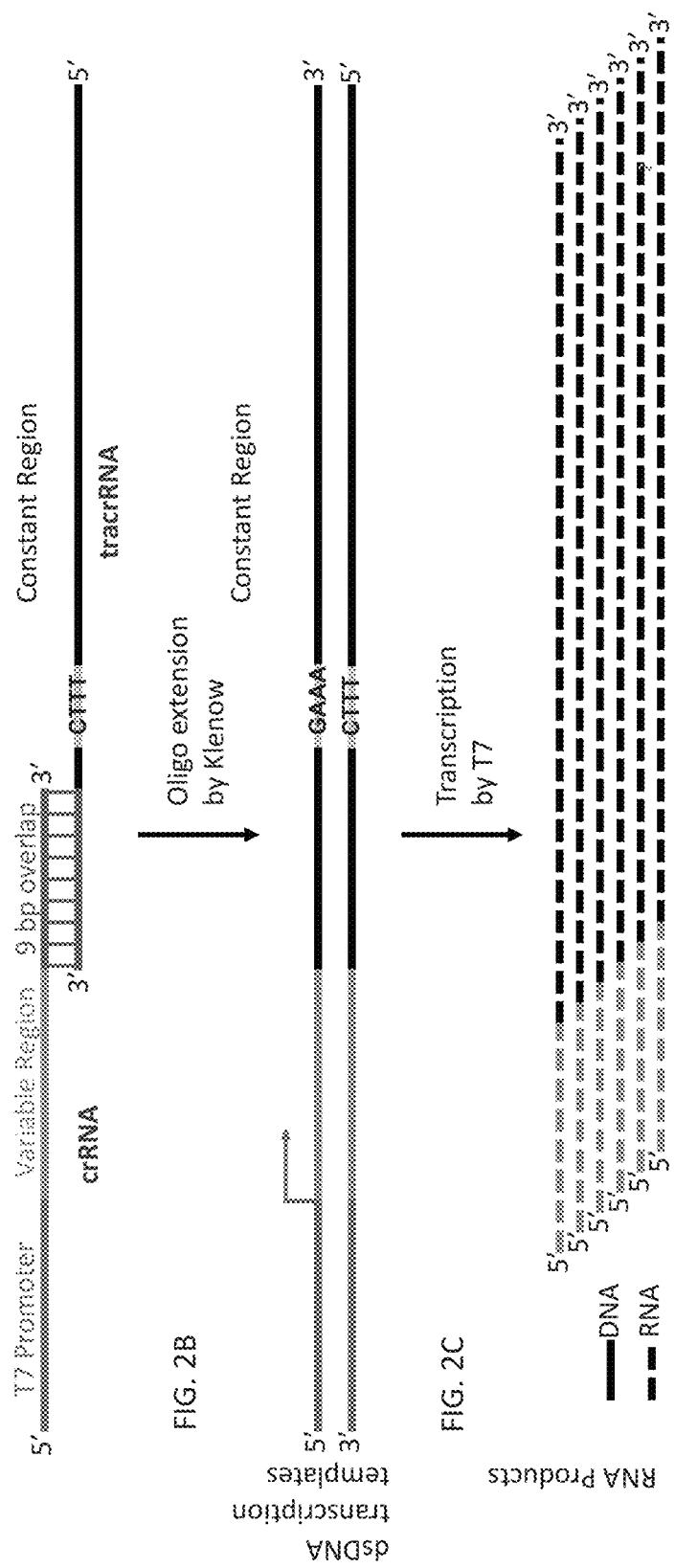

The third lane contains target DNA digested with S. pyogenes Cas9 nuclease programmed in vitro using purified reaction sgRNA products depicted in FIG. 2A-C.

The fourth lane contains target DNA digested with S. pyogenes Cas9 nuclease within the template assembly and transcription reaction as depicted in FIG. 2A-C and that also contained recombinant Cas9 nuclease protein (one step Cas 9 digest). One step refers to the reaction mixture containing the Cas nuclease while two step refers to addition of Cas nuclease to the reaction mixture after synthesis of the guide RNA.

FIG. 3A-3D shows how the reaction in FIG. 1 can be applied to making custom guide RNA in a single reaction suitable for activating as N. meningitidis Cas9 protein.

FIG. 3A shows a first ss DNA oligonucleotide containing a DNA targeting region (which corresponds to the targeting region of a single guide RNA) inserted between a T7 RNA promoter and a region for hybridizing with a second synthetic ss oligonucleotide. The first ss DNA oligonucleotide contains the sequence for the top strand of the T7RNAP promoter and a targeting region. The targeting region is the sequence by which the final guide RNA associated with Cas is directed to specific sequences in genomic DNA. The second ss DNA oligonucleotide contains the sequence corresponding to N. meningitidis tracrRNA in the sgRNA.

FIG. 3B shows that the extended oligonucleotides in FIG. 3A provide a ds DNA that can serve as a transcription template for sgRNA for N. meningitidis Cas9.

FIG. 3C shows the N. meningitidis Cas9 sgRNA transcription products of the template assembly and transcription reaction.

Figure 3D:
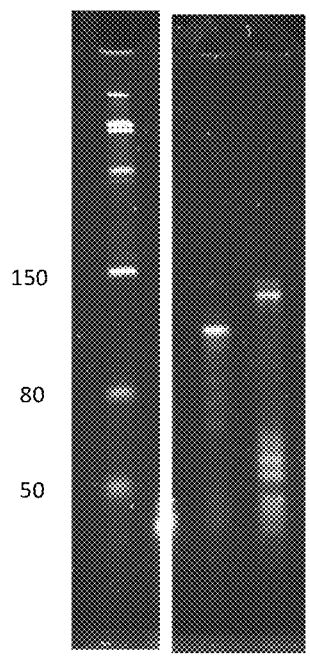

FIG. 3D shows the transcription products of long and short RNAs after treatment with DNAseI and subsequent purification. Products were separated on a denaturing 6% polyacrylamide TBE Urea gel, stained with SYBR Gold, and photographed under UV transillumination.

The first lane contains an RNA molecular size standard.

The second lane contains the purified sgRNA from the reaction using the short (96nt) second template oligonucleotide, and The third lane contains the purified sgRNA from the reaction using the longer (120nt) second template oligonucleotide.

Figure 3E:
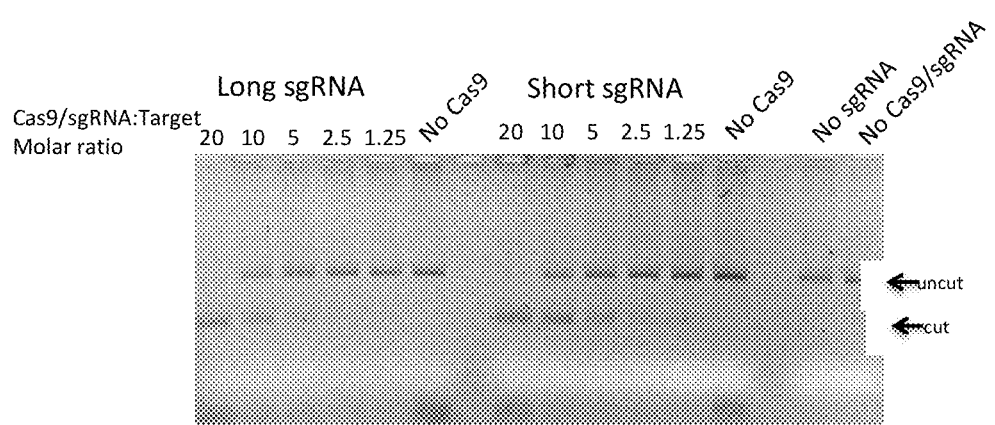

FIG. 3E shows the specific ds DNA endonuclease activity of N. meningitidis Cas9 programmed with a single guide RNA after addition of Cas nuclease to the reaction mixture containing synthesized guide RNA. The method permitted rapid analysis of the efficacy of short and long guide RNAs when combined with Cas for endonuclease cleavage. The long and short sequences differed by a 3'-extension of the sgRNA. The substrate of the cleavage reaction shown is a ~550 bp PCR product that was digested into 2 fragments of ~350 and ~200 bp after incubation with short or long sgRNA programmed Cas9 protein. Differing molar ratios of Cas9 programmed with sgRNA: target are shown as indicated for each target DNA (Nme WTAP Ex8) long (FL) and NmeWTAP Ex8 short (S)) reactions.

Digestion reactions were separated on 1.5% agarose TBE gel, stained with ethidium bromide and photographed under UV transillumination. Both long and short sgRNAs were shown to be active. An advantage of this method is the ability to rapidly test for active guide RNA sequences with little previous knowledge of what sequences would be active.

FIG. 4A-4D shows how the reaction in FIG. 1 can be applied to making custom guide RNA in a single reaction suitable for activating a S. aureus Cas9 protein.

Figures 4A, 4B, 4C:
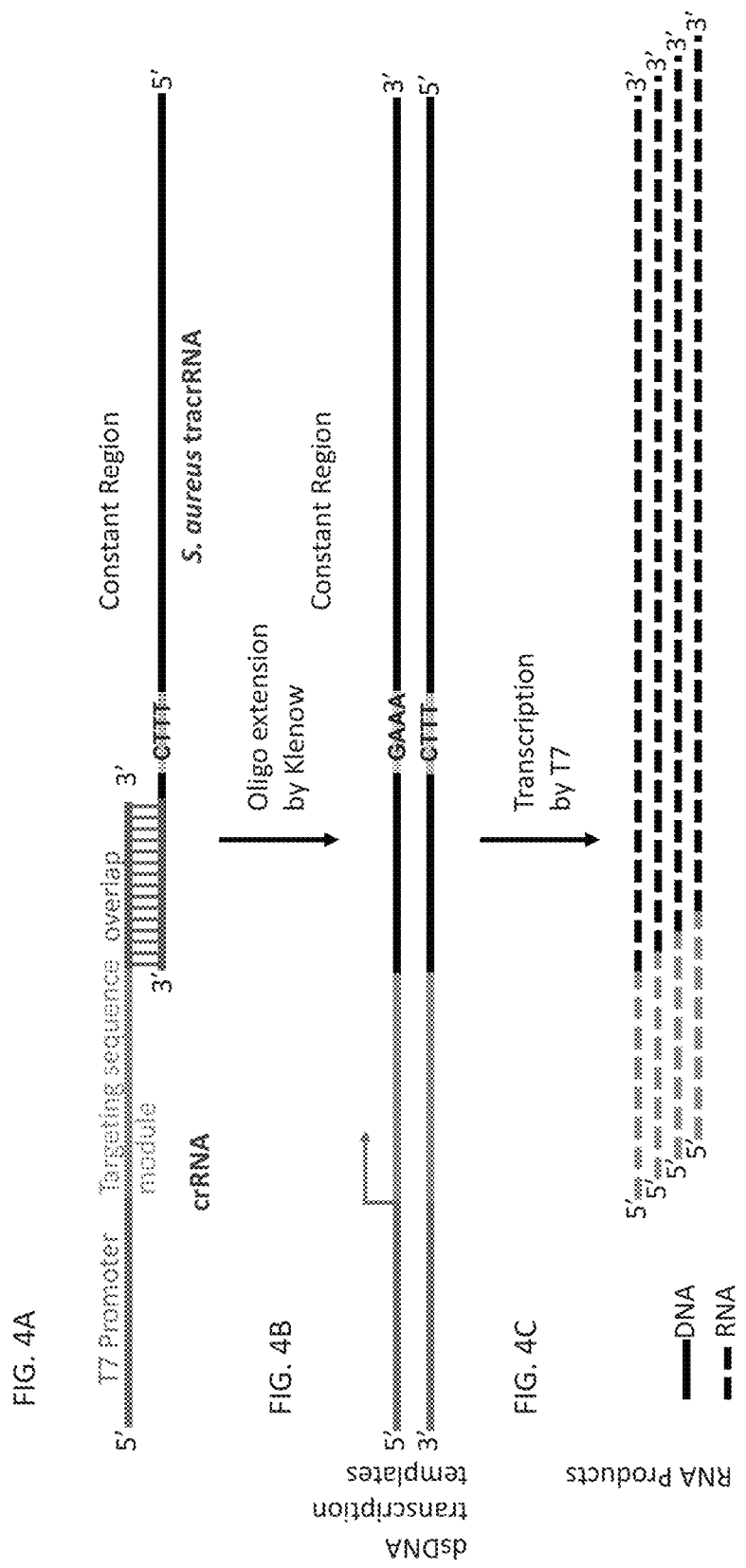

FIG. 4A is similar to FIG. 3A except the second oligonucleotide contains a sequence module for S.aureus tracrRNA.

FIG. 4B is similar to FIG. 3B except that S. aureus Tracr RNA has become part of the duplex DNA template for transcription.

FIG. 4C shows the S.aureus Cas9 sgRNA transcription products of the template assembly and transcription reaction.

Figure 4D:
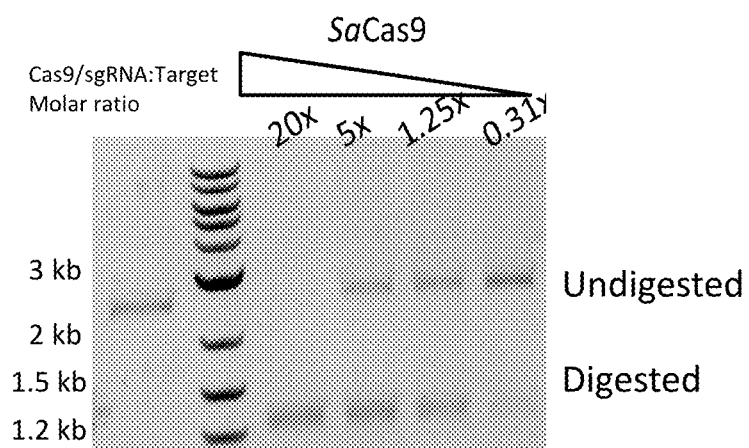

FIG. 4D shows the specificity of cleavage of a ds DNA target by S. aureus Cas9 ribonucleoprotein programmed with the single guide RNA in FIG. 4A-4C.

In FIG. 4D, the substrate is a ~2700 bp linearized plasmid DNA that is digested into 2 fragments of ~1300 after incubation with sgRNA programmed Cas9 protein. Cleavage reactions were resolved on 1% agarose TBE gels, stained with ethidium bromide and photographed under UV transillumination.

The first lane contains the target DNA incubated alone.

The second lane contains a ds DNA ladder.

The third to sixth lanes contain target DNA incubated with recombinant S. aureus Cas9 protein programmed with the products of the reaction depicted in FIG. 4A-4C. The fold excess of S. aureus Cas9/sgRNA to a constant amount of target DNA (3 nM target DNA/lane) is shown above each lane.

FIG. 5A-5E shows custom DNA template assembly and transcription of sgRNA for *Acidaminococcus* sp BV3L6 Cpf1 in a single reaction, Cpf1 programming and target DNA digestion.

FIG. 5A schematically depicts the design of ss DNA oligonucleotides for Cpf1 sgRNA template assembly and transcription. Sequence modules on the first ss DNA oligonucleotide include a T7 promoter, a constant region (tracrRNA) and a complementary region (overlap) while the second ss DNA oligonucleotide has a sequence module for targeting substrate duplex DNA and a complementary sequence.

FIG. 5B depicts the fully extended ds DNA transcription template.

FIG. 5C shows the *Acidaminococcus* sp Cas9 sgRNA transcription products of the template assembly and transcription reaction.

Figure 5D:
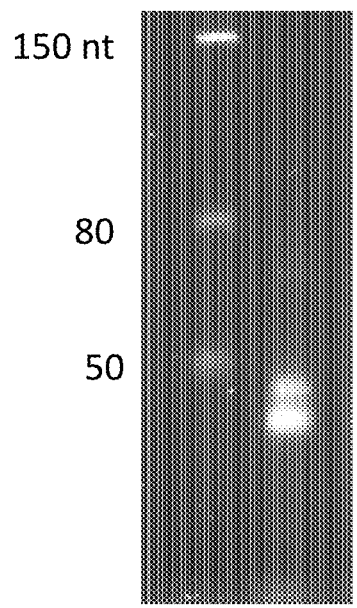

FIG. 5D shows the sgRNA produced in FIG. 5C after DNAseI and purification. Products were separated on a denaturing 6% polyacrylamide TBE Urea gel, stained with SYBR Gold, and photographed under UV transillumination. The first lane contains an RNA molecular size standard. The second lane contains the purified sgRNA from the reaction.

Figure 5E:
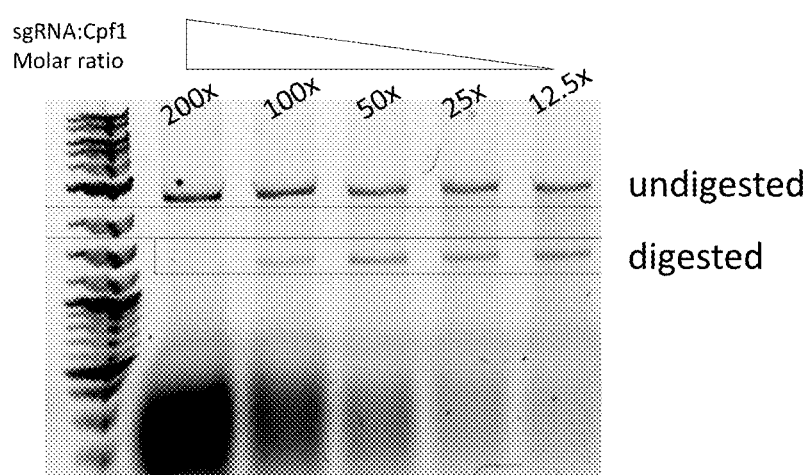

In FIG. 5E, the substrate is a ~2700 bp linearized plasmid DNA that is digested into 2 fragments of ~1300 bp after incubation with sgRNA programmed Cas9 protein.

Cleavage reactions were resolved on 1% agarose TBE gels, stained with ethidium bromide and photographed under UV transillumination. The first lane contains a ds DNA ladder with sizes as indicated. The second to sixth lanes contain target DNA incubated with recombinant *Acidaminococcus* sp BV3L6 CPF1 protein programmed with the sgRNA made as shown in FIG. 5A-5C. The fold excess of *Acidaminococcus* sp BV3L6 CPF1/sgRNA to target DNA is shown above each lane.

Figure 6A:
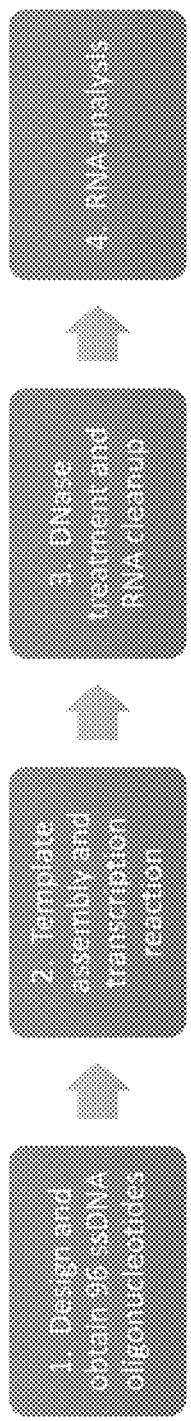
Figure 6B:
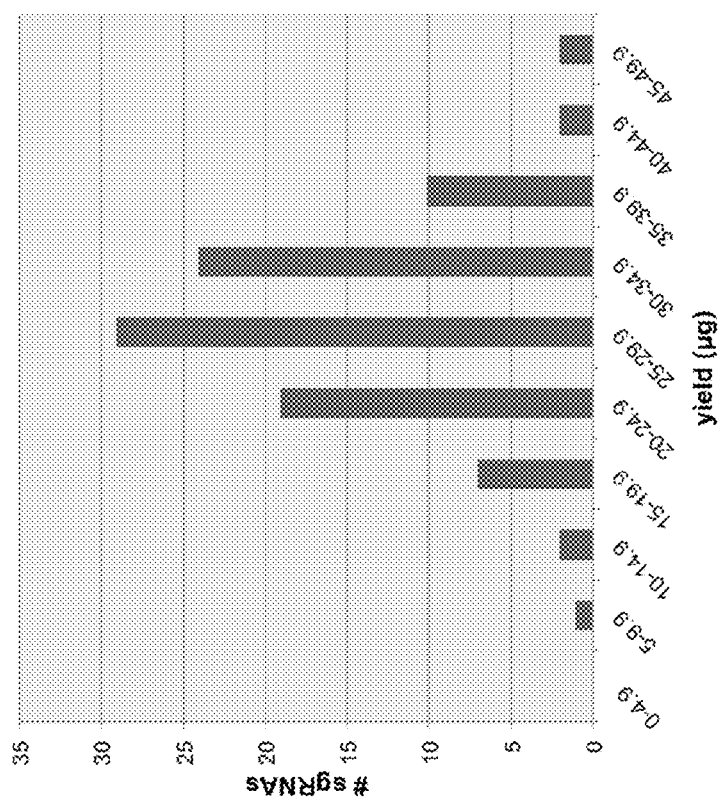

FIG. 6A-6B shows how an arrayed library of multiple single guide RNAs can be made in a highly parallel, high throughput, multiwell plate based format.

FIG. 6A depicts a workflow for the synthesis of multiple sgRNAs where (1) is design and manufacture of 96 ss DNA oligonucleotides; (2) assembly of duplex DNA and transcription; (3) cleanup of sample with DNase treatment and RNA cleanup; and (4) RNA analysis.

FIG. 6B shows the distribution of RNA yields from an experiment as outlined in FIG. 2A-2C where 96 individual synthetic ss DNA oligonucleotides were designed and procured in a 96-well plate. The 96 individual ss DNA oligonucleotides were combined with a single sequence second ss DNA oligonucleotide in a separate 96-well plate under the reaction conditions described, then purified. The yield of RNA for each of the arrayed library members was determined by spectrophotometry. The results show that variable sequences provide a range of yields under optimized conditions described in the examples. Where yield is not required to be optimized, conditions can be varied.

FIG. 7A-7D shows DNA template assembly and transcription of a functional RNA aptamer. Here the Mango RNA aptamer in a scaffold of 6S RNA is synthesized in a single reaction.

FIG. 7A shows the design of ss DNA oligonucleotide templates for assembly and transcription.

FIG. 7B shows the fully extended transcription template (duplex DNA).

FIG. 7C depicts the RNA products of the reaction.

FIG. 7D shows the activity of purified RNA mango made according to FIG. 7A-7C. The mango RNA was mixed at the concentrations provided above each lane (0, 0.5, 0.25, 0.125, 0.06 and 0.03 µM) with buffer and TO1 fluorophore. Tubes were photographed under UV transillumination. Brighter fluorescence is seen as lighter color.

FIG. 8A-8D shows how a modular functional dimeric broccoli aptamer RNA may be synthesized in a single reaction. Broccoli is a 49-nt aptamer. Dimeric broccoli is two broccoli aptamers within one long stem loop in a backbone of a scaffold sequence F30 based on the naturally occurring phi-29 viral RNA three-way junction motif. diBroccoli was inserted into each of two entry points in F30 to create F30-2xdBroccoli. Thus, this F30 scaffold presents the equivalent of four Broccoli units and is roughly four times brighter than F30-Broccoli (Svensen, et al., Cell Chemical Biology, 23:415-25, 2016).

FIG. 8A shows the design of first and second ss DNA oligonucleotides where the first ss DNA oligonucleotide contains a sequence module for a T7 promoter and the second ss oligonucleotide contains two Broccoli sequence modules with a spacer between. Complementary sequences are present at the 3' end of both oligonucleotides.

FIG. 8B shows the fully extended duplex DNA transcription template.

FIG. 8C shows the RNA transcription products.

FIG. 8D shows the activity of functional 2x diBroccoli RNA. The RNA produced according to FIG. 8A-8C was purified, and mixed at the concentrations shown (0, 0.5, 0.25, 0.125, 0.06 and 0.03 µM) with buffer and DHBF1 fluorphore. Tubes were scanned on a Typhoon multi-imager with excitation at 457 nm and emission detected at 526 nm. Brighter fluorescence is seen as darker color.

Figure 9:
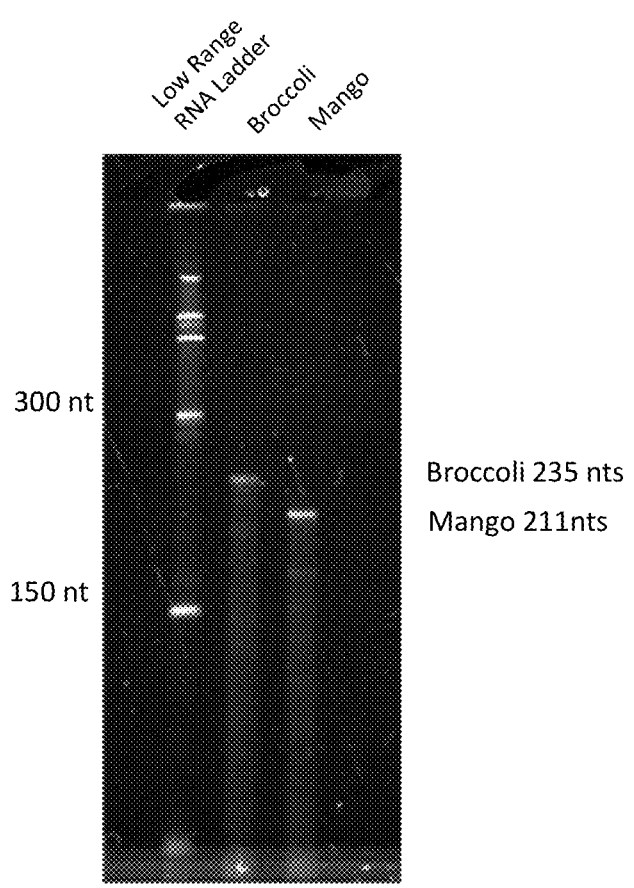

FIG. 9 shows the RNA products obtained from Example 6 and 7. Reaction products from template assembly and transcription reactions were separated by denaturing polyacrylamide gel electrophoresis, stained with SYBR Gold, and photographed under UV transillumination. The first lane contains an RNA size marker, the second lane contains Broccoli reaction products from Example 7. The third lane contains Mango reaction products from Example 6.

DETAILED DESCRIPTION OF EMBODIMENTS

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "oligonucleotide" as used herein denotes a ss multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "mixture", as used herein, refers to a combination of elements, that are interspersed and not in any particular order. Examples of mixtures of elements include a number of different elements that are dissolved in the same aqueous solution. A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "duplex," or "duplexed," as used herein, describes two complementary polynucleotides that are base-paired, i.e., hybridized together.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12, at least 15 or at least 20 nucleotides of complementarity.

The term "strand" as used herein refers to a nucleic acid made up of nucleotides covalently linked together by covalent bonds, e.g., phosphodiester bonds. In a cell, DNA usually exists in a ds form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure.

The term "hybridizing" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double strandedness under normal stringency conditions, unless the two nucleic acid strands contain a certain number of nucleotides in specific sequences which are substantially or completely complementary.

The term "extending", as used herein, refers to the extension of a nucleic acid, e.g., a primer or a primer extension product, by the addition of nucleotides using a polymerase. For example, if a primer that is annealed to a nucleic acid is extended, the nucleic acid acts as a template for extension reaction.

As used herein, the term "overlapping sequence", refers to a sequence that is complementary in two polynucleotides and where the overlapping sequence is ss, on one polynucleotide it can be hybridized to another overlapping complementary ss region on another polynucleotide. By way of example, the overlapping sequence may be complementary in at least 5, 10, 15, or more polynucleotides in a set of polynucleotides. An overlapping sequence may be at or close to (e.g., within about 5, 10, 20 nucleotides of) the 3' ends of two distinct molecules (e.g., the 3' ends of two ss oligonucleotides, or the 3' end of the top strand of first ds polynucleotide and the 3' end of the bottom strand of a second ds molecule), where, if the non-overlapping sequence is at the 3' ends then the non-overlapping sequence may be removed using a 3'-5' exonuclease activity of a polymerase. An overlapping sequence may vary in length and, in some cases, may be at least 12 nucleotides in length (e.g. at least 15, 20 or more nucleotides in length) and/ or may be up 100 nucleotides in length (e.g., up to 50, up to 30, up to 20 or up to 15 nucleotides in length).

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunological tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'- ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

Any of the enzyme listed herein may have an amino acid sequence that is identical to that of a naturally occurring enzyme, or a sequence that is at least 90% identical, e.g., at least 95% identical, to a naturally occurring enzyme.

Compositions and methods are provided herein for assembling polynucleotides from synthetic oligonucleotides in a single reaction vessel. Assembly of polynucleotides is fundamentally different from amplification of naturally occurring target polynucleotides that occur in nature within a mixture that includes non-target DNAs. In amplification, multiple rounds of oligonucleotide primer extension (in the case of DNA amplification) occur in a reaction in order to increase the quantity of or to create additional copies of a starting molecule (template) or portion of a starting molecule.

In embodiments of the invention, assembly as used herein refers to the hybridization of oligonucleotide substrates in the reaction to create a template for DNA polymerase for 3' extension of the ends of the oligonucleotides. The assembled template is a ds DNA with an RNAP promoter that can be transcribed into a novel non-natural RNA that is not encoded by the sequence of the individual input DNA oligonucleotides.

No denaturation step is required, because the inputs are less complex than a mixture of genomic DNA, or cDNA prepared from cellular total or mRNA prepared using random priming, oligo d(T) priming or other cDNA synthesis priming strategies that produce complex mixtures of cDNA. The oligonucleotide templates are designed so that annealing occurs efficiently at room temperature.

No DNA amplification takes place in the method, and no purified genomic DNA, or cDNA prepared from RNA derived from biological sources is used. Instead, the method uses relatively small, synthetic DNA oligonucleotide that do not occur in nature and that contain functional sequence modules that may or may not be derived from nature to assemble larger purpose-designed polynucleotides.

One feature of present embodiments is the use of an RNAP promoter and RNAP such as any RNAP and promoter known in the art. Certain examples herein not intended to be limiting, describe the use of T7 RNAP and T7 RNAP promoter. Other examples of polymerases with promoters include T7 RNAP with T7 Class III RNAP promoter or T7 phi 2.5 RNAP promoter, SP6 RNAP with SP6 RNAP promoter, T3 RNAP with T3 RNAP promoter, Syn5 RNAP with Syn5 RNAP promoter, E. coli RNAP with T5 promoter, E. coli RNAP with a standard E. coli promoter that is active in vitro e.g. TTGACAN(17)TATAAT (SEQ ID NO:1), or Tac promoter and promoters recognized by thermostable RNAPs (New England Biolabs, Ipswich, Mass.). Commonly used phage RNAPs for use herein are usually specific for promoters in their genomes. However, some phage promoters use host RNAP. See above example of T5 promoter with E. coli RNAP.

One feature of present embodiments is a DNA polymerase. Embodiments utilize mesophilic DNA polymerases such as T4 DNA polymerase. E. coli DNA polymerase I Klenow fragment exo minus, and E. coli DNA polymerase I Klenow fragment. Other polymerases include Family B DNA polymerases such as Pfu DNA polymerase, Q5, Phusion, Family A DNA polymerases such as E. coli DNA polymerase I, Taq, and Taq variants including HemoKlentaq, Bst DNA polymerase, and strand displacing DNA polymerases such as Sulphololobus, and Bst variants such as Bst 2.0, Bst 3.0, or Phi29 (the specific identified polymerases are available from New England Biolabs, Ipswich, Mass.).

The design of the synthetic ss DNA oligonucleotides requires an overlapping region of complementary bases. The number of nucleotides in an overlapping region is in the range of at least 5 nucleotides to as long as practical because of cost constraints. For example, embodiments include ranges of lengths of overlapping sequences include 5 nucleotides (nt)-50 nt or 5 nt-40 nt, or 5 nt-35 nt, or 5 nt-30 nt or 5 nt-25 nt.

The size of ss oligonucleotides fragments for joining to form a long polynucleotide is limited only by the length of oligonucleotide that is cost efficient to synthesize in the upper range and by a size suited to incorporate an RNAP promoter and a region of overlap in the lower range. For example, a single oligonucleotide might be 20-500 nts in length for example 20-200 nts for example 20-150 nts in length.

Once joined, the newly synthesized RNA may be of any desired size. In a preferred embodiment, the shortest synthetic fragment made from two oligonucleotides would be 18 nt and the largest would be approximately double the maximum size of an oligonucleotide that is capable of being synthesized in a cost effective manner for example, about 1000 nt. Examples include 18 nt-393 nt or 25 nt-350 nt or 40 nt-300 nt or 60 nt-260 nt. Multimers of synthetic fragments can be joined by ligation or other means to form a polynucleotide of any desired length.

Examples of RNA that can be synthesized by the present methods or using the present compositions include guide RNA, aptamers, mRNAs, tRNAs, microRNAs, shRNAs, snRNAs, small non-coding RNAs, RNA probes, ribozymes or any other type of RNA as desired.

In embodiments of the invention, all the reagents for assembling a single DNA molecule from synthetic oligonucleotides and also for transcription of the DNA molecules into RNA molecules are provided in a single reaction mixture.

In embodiments of the invention, guide RNA can be made from joined and transcribed ss synthetic oligonucleotides in a single reaction mixture that additionally includes the Cas enzyme to which the guide RNA attaches to enable the complex to act as a sequence specific nuclease in the presence of a DNA target additionally added to the reaction mixture. We demonstrated this by showing cleavage of template DNA resulting from incorporation of sgRNA into Cas9 (programming) in Example 1 and FIG. 2A-2F.

This is significant because the method markedly shortens current workflows and reduces expense for in vitro programming of Cas9. This is achieved by using inexpensive and rapidly obtainable ss DNA oligonucleotides as substrate inputs as compared to commercially assembled ds DNA constructs such as gBlocks (IDT, Coralville, Iowa) or genestrings (Life Technologies, Carlsbad, Calif.) which take longer to obtain and may require amplification because they are supplied at low concentration. As compared to producing plasmid DNA templates for sgRNA synthesis, the workflow of the current method is much shorter. Finally, in contrast to costly and not rapidly obtainable commercially synthesized RNA oligonucleotides (IDT, GE Dharmacon, Lafayette, Colo.), the ss DNA oligonucleotides used herein are significantly less costly and more efficient to obtain for commercial use.

The programming of Cas9 nuclease within the sgRNA template assembly and transcription reaction is significant because this allows for the rapid and inexpensive creation of sequence-specific ds DNA endonucleases in a one-step reaction by adding a relatively short, inexpensive, and readily available custom ss DNA oligonucleotide. In essence, this method allows one to create a custom endonuclease capable of cutting almost any sequence and suitable for recombinant DNA manipulation (e.g. molecular cloning of DNA fragments) in minutes.

For sgRNA programming of Cas9 or Cas9 ortholog proteins, a target region denotes a specific nucleic acid sequence to which a Cas nuclease is directed for cutting, nicking or binding that is determined by the sequence of the guide RNA and protospacer adjacent motif (PAM) sequence requirements of the Cas9 or Cas9 ortholog protein.

Assembly of a plurality of oligonucleotides into a duplex DNA that can be transcribed to a single RNA in a single reaction chamber and in a single reaction step has many uses. For example, it is possible to assemble large RNA molecules from more than two ss oligonucleotides. In the figures and examples provided herein, some sequence modules are described on the first ss DNA oligonucleotide and other sequence modules are described on the second ss DNA oligonucleotide. However, the assembly method is not dependent on the order in which the sequence modules occur. They might be switched around as determined to be optimal by the intended use. Indeed in FIG. 5A-5E the targeting sequence module is on the second ss DNA oligonucleotide whereas in FIG. 4A-4D, the targeting sequence module is on the first ss oligonucleotide.

Single RNA molecules of varying lengths may be transcribed from assembled duplex DNA where the limitation of length of ss DNA oligonucleotides is limited only by the cost and efficiency of synthesis of the oligonucleotides, Alternatively, 4 oligonucleotides or more generally 2 oligonucleotides may be assembled in which the pairs of oligonucleotides may become assembled after hybridization of complementary sequences at their 3' ends. In addition the second oligonucleotide may hybridize to a third oligonucleotide by complementary sequences at the 5' end. A strand displacing polymerase may read through the third and fourth ss DNA oligonucleotide resulting in an extended duplex DNA and when transcribed are large RNA. Alternatively, a non strand displacing polymerase may be utilized to complete the duplex where a ligase is added to close nicks.

Because any sequence can be designed for ss DNA oligonucleotide synthesis, it is possible to design sequence modules which may be characterized by their function within the ss DNA oligonucleotide sequence. The sequence modules may be fixed for a population of ss DNA oligonucleotides or may contain sequences that vary by design or randomly with the population. In this way, assembled DNA duplexes and transcribed RNA may represent a diverse population wherein members have variable and fixed sequence modules, and may be of any desired length.

One application of the described method of assembling duplex DNA and transcribing RNA in a single step reaction is to generate guide RNAs. Another application is to generate RNA aptamers that may react with a detectable marker or may react with another sequence module to generate a signal. This is illustrated herein with mango and broccoli aptamers. These aptamers are suited for demonstrating the utility of the method as they readily bind a detector dye. However, the assembly method described herein may be generally applicable to other biological markers that involve RNA molecules.

In some embodiments, it may be desirable to immobilize one or more of the ss DNA oligonucleotides or the transcribed RNA before, during or after the assembly reaction. Immobilization may occur by means of coated or uncoated beads, microwell dishes, columns, papers, microfluidic devices etc. Immobilization may occur through affinity binding of the DNA or RNA by means of a modified nucleotide or biotin/streptavidin binding or other affinity binding molecule.

Kits

Also provided by this disclosure is a kit for practicing the subject method, as described above. A kit may contain any combination of the reagents described above, e.g., oligonucleotides, dNTPs, riboNTPs, DNA polymerase, RNA polymerase, etc. The various components may be in different containers or in the same container.

In addition, the kit may also comprise reagents for performing the reaction, e.g., one or more buffers. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the present method may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

All references cited herein are incorporated by reference.

EXAMPLES

Aspects of the present teachings can be further understood in light of the following examples, which should not be construed as limiting the scope of the present teachings in any way.

Description of Terms

Clustered Regularly Interspersed Short Palindromic Repeats Array (CRISPR).

CRISPR RNA (crRNA): A small RNA arising from transcription and processing of a CRISPR array. crRNA interacts with tracrRNA and Cas9 to direct the sequence specific binding of the complex.

Trans-activating crRNA (tracrRNA): A small non-coding RNA transcribed from the CRISPR locus. The tracrRNA base pairs with a crRNA. The crRNA and tracrRNA complex is incorporated into Cas9 proteins to enable cleavage of target sequences Single guide RNA (sgRNA): A synthetic fusion of a crRNA and tracrRNA, often connected by a GNRA tetraloop sequence that provides both targeting specificity and scaffolding/binding ability for Cas9 nuclease in a single polynucleotide (Jinek et al. (2012) Science, 337(6096):816-21).

Cas: CRISPR-associated genes.

Cas9, Csn1: a CRISPR-associated protein containing two nuclease domains, that is programmed by small RNAs to cleave DNA Nuclease-deficient Cas9 (dCAS9).

Cpf1: A naturally occurring two-component RNA programmable DNA nuclease (class 2) lacking tracrRNA, associated with CRISPR. It utilizes a T-rich protospacer-adjacent motif. Moreover, Cpf1 cleaves DNA via a staggered DNA ds break. It is obtainable from *Acidaminococcus*.

Template refers to DNA that is used for RNA synthesis.

All reagents can be obtained commercially from New England Biolabs, Ipswich, Mass. unless stated otherwise. Exemplary conditions for assembly reactions of two oligonucleotides used in the present examples In some cases, the reaction may be done in a single closed vessel, without changing the conditions of the reaction, opening the vessel or adding additional reagents during the course of the reaction.

Example 1

Custom *S. pyogenes* sgRNA DNA Template Assembly and Transcription in a Single Reaction and Cas9 Programming in a Single Reaction A 49 nt ss DNA oligonucleotide synthesized from three functional modules: (a) the top strand of the T7 RNAP promoter; (b) coding strand of a 20 nt region corresponding to a targeting region, of an sgRNA; and (c) a region of 9 nt corresponding to the repeat region of the *S. pyogenes* CRISPR repeat was added to a reaction containing a second ss DNA oligonucleotide corresponding to the template strand of the *S. pyogenes* tracrRNA connected to the remainder of the *S. pyogenes* CRISPR repeat by a GAAA tetraloop sequence (FIG. 2A) (Jinek, et al. (2012) Science, 337(6096): 816-21). The first and second ss DNA oligonucleotides were complementary to each other for 9 bp at their 3'ends.

The reaction was carried out by combining the oligonucleotides, enzymes, and buffers as follows:

(a) 0.62 units (0.05-5 units) *E. coli* DNA polymerase I Klenow fragment; 0.25 uM first synthetic or natural polynucleotide and 0.25 uM second synthetic or naturally occurring polynucleotide although oligonucleotides may be added in at any convenient concentration, 33 um (1-100 micromolar) dNTP, T7 RNAP and buffers such as provided by NEB in its HiScribe™ kit (New England Biolabs, Ipswich, Mass.) . Incubation in the core reaction mixture was 37° C. for 30 minutes for convenience although as little as 1 minute or as much as 4 hours or up to overnight incubation can be used.

(b) Cas9 capable of reacting with sgRNA to form a complex with nuclease activity.

(c) Addition of target DNA for nuclease cleavage (a), (b) and (c) can be performed separately (Example 1-6).

(a), and (b) can be carried out together in one tube and in a single incubation followed by (c).

(a), (b) and (c) can be carried out together in one tube and in a single incubation (Example 1).

Template assembly occurred via annealing of the 2 oligonucleotides and their extension by *E. coli* DNA polymerase I Klenow fragment (FIG. 2B). Transcription was initiated as ds DNA was formed in the reaction (FIG. 2C). sgRNA was purified, analyzed by gel electrophoresis (FIG. 2D) and used for programming recombinant Cas9 nuclease (FIG. 2E) where Cas9 was combined with sgRNA in a second step to cleave a target DNA.

To assess the function of the sgRNA synthesized by the method, equimolar sgRNA was mixed with Cas9 nuclease (30 nM final concentration) in Cas9 reaction buffer (NEB 20 mM HEPES pH 6.5, 100 mM NaCl, 5 mM $MgCl_2$, 0.1 mM EDTA) for 10 minutes at 25° C. Target DNA (3 nM 514 bp PCR product) was added followed by a further incubation at 60 minutes at 37° C. The results are shown in FIG. 2E.

When Cas9 was added to the assembly and transcription reaction mixture at the outset, an excess of guide RNA was generated by the synthesis reaction for programming Cas9 nuclease directly in the reaction mixture described above which also contained target DNA (3nM linearized PBR322). The results are shown in FIG. 2F which demonstrated that template assembly, transcription, loading of sgRNA into Cas9 protein, and cleavage of target DNA occurred in the single reaction.

Example 2

Custom *N. meningitidis* sgRNA DNA Template Assembly and Transcription in a Single Reaction A 60 nt ss DNA oligonucleotide containing three sequence modules: (a) the first strand of the T7 RNAP promoter; (b) coding strand of a 22 nt region corresponding to a targeting region, of an sgRNA; and (c) a region of 15 nt corresponding to the repeat region of the *N. meningitidis* CRISPR repeat; was added to a reaction containing a second ss DNA oligonucleotide corresponding to the template strand of the *N. meningitidis* tracrRNA connected to the remainder of the *N. meningitidis* CRISPR repeat by a GAAA tetraloop sequence (FIG. 3A) (Esvelt KM, et al. (2013), Nature Methods 10: 1116-1121). The first and second ss DNA oligonucleotides were complementary to each other for 15 bp at their 3'-ends. Long (120 nt) and short (96 nt)

versions of the second oligonucleotide were used to make long or short versions of the sgRNA. The long and short sgRNAs differed by a 3'-exension of their sequence.

The oligonucleotides were combined with enzymes, and buffer as described in Example 1 in a reaction vessel and incubated at 37° C. for 30 minutes. Template assembly occurred via annealing of the 2 oligonucleotides and their extension by E. coli DNA polymerase I Klenow fragment (FIG. 3B). Transcription began as ds DNA was formed in the reaction (FIG. 3C). sgRNA was purified, analyzed by gel electrophoresis (FIG. 3D) and used for programming recombinant Cas9 nuclease (FIG. 3E).

To assess the function of sgRNA synthesized by the method, the sgRNA was mixed with recombinant N. meningitidis Cas9 nuclease in Cas9 reaction buffer (NEB, 20 mM HEPES pH 6.5, 100 mM NaCl, 5 mM $MgCl_2$, 0.1 mM EDTA) for 10 minutes at 25° C. and substrate DNA was added followed by a further incubation at 60 minutes at 37° C. The results are shown in FIG. 3E.

The results showed that the assembly method can be used for the rapid production of sgRNAs for Cas9 orthologs that are not commercially available or in wide use. In this case both the long and short versions of the sgRNA synthesized supported the specific ds DNA endonuclease activity of N. meningitidis Cas9. Significantly, the approach described here will be useful in cases where the sequences of the regions required for Cas9 ortholog function are not known and where rapid prototyping of sgRNA sequence and structure are desirable.

Example 3

Custom S. aureus sgRNA DNA Template Assembly and Transcription in a Single Reaction A 58 nt ss DNA oligonucleotide containing three functional modules: (a) the first strand of the T7 RNAP promoter, (b) the coding strand of a 22 nt region corresponding to a targeting region of an sgRNA; and (c) a region of 15 nt corresponding to the repeat region of the S. aureus CRISPR repeat; was added to a reaction containing a second ss DNA oligonucleotide that was 77 nt in length, corresponding to the template strand of the S. aureus tracrRNA connected to the remainder of the S. aureus CRISPR repeat by a GAAA tetraloop sequence (FIG. 4A). The first and second ss DNA oligonucleotides were complementary to each other for 15 bp at their 3' ends.

Reactions were carried out by combining the oligonucleotides, enzymes, and buffers as described and incubating at 37° C. for 30 minutes. Template assembly occurred via annealing of the 2 oligonucleotides and their extension by E. coli DNA polymerase I Klenow fragment (FIG. 4B). Transcription began as ds DNA is formed in the reaction (FIG. 4C). sgRNA was purified and used for programming recombinant Cas9 nuclease (FIG. 4D).

To assess the function of sgRNA synthesized by the method, the sgRNA was mixed with recombinant S. aureus Cas9 nuclease in Cas9 reaction buffer (NEB, 20 mM HEPES pH 6.5, 100 mM NaCl, 5 mM $MgCl_2$, 0.1 mM EDTA) for 10 minutes at 25° C. and substrate DNA was added followed by a further incubation at 60 minutes at 37° C. The results are shown in FIG. 4D.

This is another example of how the method can be used for the rapid production of sgRNAs for Cas9 orthologs other than S. pyogenes that are not commercially available or in wide use and for which synthetic RNA oligonucleotides corresponding to tracr and crRNAs, or other transcription templates are not commercially or readily available.

Example 4

Custom *Acidaminococcus* sp BV3L6 CPF1 sgRNA DNA Template Assembly and Transcription in a Single Reaction A 43 nt ss DNA oligonucleotide containing two functional modules: (a) top strand of the T7 RNAP promoter, and (b) a coding strand of a 20 nt region corresponding to a direct repeat of the *Acidaminococcus* sp BV3L6 Cpf1 CRISPR repeat was added to a reaction containing a second ss DNA oligonucleotide 35 nt in length and corresponding to the template strand of the partial *Acidaminococcus* sp BV3L6 Cpf1 CRISPR repeat and a 20 nt targeting region. The 3' ends of the first and second ss DNA oligonucleotides were complementary for 15 bp, and together form a template for a complete *Acidaminococcus* sp BV3L6 Cpf1 sgRNA (FIG. 5A) (Zetsche et al. (2015) Cell. 163: 1-22). No GAAA tetraloop linker was required as the Cpf1 guide RNAs are single polynucleotides.

Reactions were carried out by combining the oligonucleotides, enzymes, and buffers as described and incubating at 37° C. for 30 minutes. Template assembly occurred via annealing of the 2 oligonucleotides and their extension by E. coli DNA polymerase I Klenow fragment (FIG. 5B). Transcription began as ds DNA was formed in the reaction (FIG. 5C). sgRNA was purified, analyzed by gel electrophoresis (FIG. 5D) and used for programming recombinant Cpf1 nuclease (FIG. 5E).

To assess the function of sgRNA synthesized by the method, the sgRNA was mixed with recombinant *Acidaminococcus* sp BV3L6 Cpf1 nuclease in NEBuffer 4 (New England Biolabs, Ipswich, MA) for 10 minutes at 25° C. and substrate DNA was added followed by a further incubation at 60 minutes at 37° C. The results are shown in FIG. 5E.

This example demonstrates that the method is versatile and can be used for the rapid production of sgRNAs for Cpf1 type RNA-guided nucleases. Furthermore the method can be used in cases where the targeting region of the resulting sgRNA is non-adjacent to the RNAP promoter and where synthetic RNA oligonucleotides useful as guide RNAs, or other transcription templates are not commercially or readily available.

Example 5

Synthesis of an Arrayed S. pyogenes Cas9 sgRNA Library using DNA Template Assembly and Transcription in Parallel Reactions An arrayed library of S. pyogenes Cas9 sgRNAs was generated as follows: A workflow is shown in FIG. 6A. 96 distinct 54-56 nt ss DNA oligos were obtained from IDT (Coralville, Iowa) and arrayed in a 96-well plate (one oligonucleotide per well). The ss DNA oligonucleotides correspond to the top strand of the T7 RNAP promoter, coding strand of a 20 nt region which differ in each of the 96 oligonucleotides (taking the place of the targeting region of an sgRNA) and a region of 14 nt complementary to the repeat region of the S. pyogenes CRISPR repeat, and were added to a reactions containing a second ss DNA oligonucleotide, common to each of the 96 reactions, corresponding to the template strand of the S. pyogenes tracrRNA connected to the remainder of the S. pyogenes CRISPR repeat connected by a GAAA tetraloop sequence (FIG. 6A-6B).

Reactions were carried out in wells of a 96-well plates by combining the oligonucleotides, enzymes, and buffers as described and incubating at 37° C. for 30 minutes. Template assembly occurred via annealing of the 2 oligonucleotides and their extension by E. coli DNA polymerase I Klenow fragment. Transcription began as ds DNA is formed in the reaction.

Each member of the RNA library resulting from transcription reactions was treated with DNaseI, purified, and yield measured and shown in FIG. 6B.

This example is significant because it demonstrates the utility of the method for rapidly and inexpensively creating arrayed libraries of sgRNAs for use in screening. Libraries could have as few as 2 members, and as many as practical restraints would allow. For example, the number of ss DNA oligonucleotide inputs, or subsequent transfection or in vitro assays. For example, 96-well, 384-well, or 1536-well plates.

Example 6

Synthesis of Functional RNA Mango Aptamers using DNA Template Assembly and Transcription in Single Reactions RNA Mango is a 29 nt guanosine quadruplex containing RNA aptamer that was selected to bind a modified thiazole orange derivative with high affinity (3.4 nM) (Dolgosheina, et al. ACS Chem Biol. 2014;9: 2412-2420).

RNA Mango used in conjunction with thiazol orange derivatives have been used as both affinity purification tools, and tools for visualization of RNA (Dolgosheina, et al. 2014). RNA mango is commonly used within the context of a larger RNA scaffold, and in particular the 6S RNA from bacteria.

In this example, RNA mango in the context of 6S RNA was synthesized from 2 ss DNA oligonucleotides in one-step DNA template assembly and transcription reactions. The first and second ss DNA oligonucleotides had 15 nt regions at their 3' termini that were complementary to each other. A first ss DNA oligonucleotide, 48 nt in length, comprising the top strand of the T7 RNAP promoter and the partial coding strand of the 6S RNA mango construct were combined with a second ss DNA oligonucleotide, 200 nt in length, made up of the template strand of the remainder of 6S mango under conditions detailed above (FIG. 7A).

Reactions were carried out by combining the oligonucleotides, enzymes, and buffers as described above and incubating the reaction mixture at 37° C. for 30 minutes. Template assembly occurred via annealing of the 2 oligonucleotides and their extension by an E. coli DNA polymerase I Klenow fragment (FIG. 7B). Transcription began as ds DNA was formed in the reaction (FIG. 7C). The 211 nt RNA products of the reaction were purified, analyzed by gel electrophoresis (FIG. 8A-8D).

To demonstrate the function of the 6S RNA mango aptamer, differing concentrations of 6S RNA mango were dispensed into tubes in an 8 well strip in a buffer containing 10 mM Tris HCl pH 7.5, 160 mM KCl, and 1 micromolar TO1. After mixing, the tubes were photographed on a UV transilluminator with a 312 nm light source (FIG. 7D). Functional 6S Mango RNA was indicated by fluorescence and was evident in the tubes containing RNA products from the template assembly and transcription reaction.

It was concluded that the 211 nt configuration of RNA mango was functional in conjunction with the TO1 thiazole orange compound. RNA mango induced the fluorescence of TO1 upon binding. The results suggest that RNA mango made in this way will be useful for detection and visualization of RNA.

Example 7

Synthesis of Functional RNA Broccoli Aptamers using DNA Template Assembly and Transcription in Single Reactions RNA broccoli is an aptamer that binds to and activates the small molecule fluorophore DHBF1. RNA broccoli-DHBF1 complexes are mimics of green fluorescent protein that can be used for RNA tagging and detection, and localization by imaging (You, et al. 2015, Annu Rev Biophys. 2015; 44: 187-206).

An RNA containing 2 copies of diBroccoli in a scaffold of F30 RNA (Filonov et al 2015 2015, Chem Biol. 2015;22: 649-660) was synthesized as described above. The first and second ss DNA oligonucleotides had 15 nt regions at their 3'-termini that were complementary to each other. A first ss DNA oligonucleotide, 72 nt in length, made up of the top strand of the T7 RNAP promoter and the partial coding strand of the F30 diBroccoli RNA was combined with a second ss DNA oligonucleotide, 200 nt in length, made up of the template strand of the remainder of F30 diBroccoli RNA under conditions detailed above and FIG. 8A.

Reactions were carried out by combining the oligonucleotides, enzymes, and buffers as described in Example 1 and incubated at 37° C. for 30 minutes. Template assembly occurred via annealing of the 2 oligonucleotides and their extension by E. coli DNA polymerase I Klenow fragment (FIG. 8B). Transcription began as ds DNA was formed in the reaction (FIG. 8C). The 235 nt RNA products of the reaction were purified, and analyzed by gel electrophoresis (FIG. 9).

To demonstrate the function of the F30 diBroccoli RNA, differing concentrations of the reaction products were dispensed into tubes in an 8 well strip in a buffer containing 10 mM Tris HCl pH 7.5, 160 mM KCl, and 1 micromolar DHBF1. After mixing, the tubes were scanned on a Typhoon multiimager with excitation at 457 nm and emission detected at 526 nm (FIG. 8D). Functional F30 diBroccoli is indicated by fluorescence and is evident in the tubes containing RNA products from the template assembly and transcription reaction. In this case the image is inverted so that stronger fluorescence appears as a darker shade.

These examples are significant because they demonstrate the usefulness of the method for the rapid generation of functional aptamer RNAs from readily available and inexpensive ss DNA oligonucleotide starting material. We envision that in addition, to RNA aptamer production, that this method is useful for generating pools of aptamers for selection, and for rapid prototyping and testing of aptamer variants including minimers, functional modules, scaffold variants, and aptamers that contain modified nucleotides.

Example 8

Synthesis of a Pooled *S. pyogenes* Cas9 sgRNA Library using DNA Template Assembly and Transcription in a Single eaction In this example the method is used to a produce a pooled library of *S. pyogenes* Cas9 sgRNAs. A pool of 54 nt first ss fragment. Transcription begins as ds DNA is formed in the reaction (FIG. 2A-2C).

This example demonstrates the utility of rapidly and inexpensively creating pooled libraries of sgRNAs for use in screening. Such libraries may include as few as 2 members, and as many as practical restraints would allow (i.e. the scale of ss DNA oligonucleotide input and size of template assembly and transcription reaction required for complete representation in sgRNA libraries of templates with extensive diversity). This example also could be extended for use in screening a pool of sequences encoding any functional RNA module. For example, RNA aptamer variants, RNA stability elements, RNA targeting elements, target sites for protein binding, and so on.

```
SEQUENCE LISTING

<160> NUMBER OF SEQ ID NOS: 1

<210> SEQ ID NO 1
<211> LENGTH: 29
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (7)..(23)
<223> OTHER INFORMATION: n is a, c, g, or t

<400> SEQUENCE: 1
ttgacannnn nnnnnnnnn nnntataat                                        29
```

DNA oligonucleotides can be synthesized that each contain a DNA sequence module that corresponds to top strand of the T7 RNAP promoter site, a sequence module that corresponds to a 20 nt-22 nt targeting sequence for sgRNA being suitable for recognizing a duplex DNA target site and a region of 14 nt complementary to the repeat region of the *S. pyogenes* CRISPR repeat. In this example, 2 or more (up to $4^{22}$) ss DNA oligonucleotides are synthesized each containing a different 20 nt-22 nt targeting region (although there is in fact no upper limit on the number that might be synthesized as needed). The library of first ss DNA oligonucleotide can then be added to a reaction mixture containing a second ss DNA oligonucleotide that contains the sequence module for the template strand of the *S. pyogenes* tracrRNA linked to the remainder of the *S. pyogenes* CRISPR repeat by a GAAA tetraloop sequence. First ss DNA oligonucleotides can be commercially obtained from synthetic oligonucleotide service providers (e.g. IDT) as pooled ss DNA oligonucleotides, or alternatively can be obtained separately and then pooled before combining with a second ss DNA oligonucleotide as described in the method.

Reactions are carried out by combining the oligonucleotides, enzymes, and buffers as described in Example 1 and incubating at 37° C. for 30 minutes. Template assembly occurs via annealing of one of the first oligonucleotides variants with one copy of the second oligonucleotides and their extension by *E. coli* DNA polymerase I Klenow

What is claimed is:

1. A method for producing a Cas nuclease/guide RNA complex, comprising:
    (a) combining:
        a DNA polymerase,
        an RNA polymerase,
        a first synthetic single stranded (ss) DNA oligonucleotide,
        a second synthetic single stranded (ss) DNA oligonucleotide,
            wherein the first ss DNA oligonucleotide comprises a promoter sequence for the polymerase and a sequence at the 3' end that hybridizes to a complementary sequence in the second ss DNA oligonucleotide;
        dNTPs,
        rNTPS, and
        a Cas nuclease, to produce a reaction mix; and
    (b) incubating the reaction mix to produce a Cas nuclease/guide RNA complex that comprises a guide RNA that is at least partially transcribed from the second oligonucleotide.
2. The method according to claim 1, further comprising adding a ligase and a third synthetic single stranded (ss) DNA oligonucleotide to the reaction mix before step (b), wherein the third ss DNA oligonucleotide comprises a sequence at the 5' end that hybridizes to a complementary sequence in the second ss DNA oligonucleotide and the guide RNA is at least partially transcribed from the second oligonucleotide and the complement of the third oligonucleotide.

3. The method according to claim 1, wherein the DNA polymerase is a strand displacing polymerase.

4. The method according to claim 1, wherein the first ss DNA oligonucleotide contains a sequence module in which the sequence is variable.

5. The method according to claim 4, wherein the variable sequence module is DNA targeting sequence for a Cas nuclease.

6. The method according to claim 1, wherein the method comprises producing a plurality of said reaction mixes in a multiwell plate, wherein the sequence of the first ssDNA oligonucleotide differs in each reaction mix.

7. The method according to claim 6, wherein the second ss DNA oligonucleotide is the same in each reaction.

8. The method according to claim 5, wherein the second ss DNA oligonucleotide comprises a tracrRNA sequence.

* * * * *